United States Patent
Tag Elsir Abd Alla

(10) Patent No.: US 10,987,382 B2
(45) Date of Patent: Apr. 27, 2021

(54) SOLANUM DUBIUM SEEDS AND HONEY (EXTRACTED FROM BEE HIVES IN ACACIA TREE POPULATED AREA) COMBINATION FOR TREATMENT OF ASTHMA AND BRONCHIAL ASTHMA

(71) Applicant: Iman Tag Elsir Abd Alla, Khartoum (SD)

(72) Inventor: Iman Tag Elsir Abd Alla, Khartoum (SD)

( * ) Notice: Subject to any disclaimer, the term of this patent is extended or adjusted under 35 U.S.C. 154(b) by 358 days.

(21) Appl. No.: 15/568,452

(22) PCT Filed: Apr. 24, 2015

(86) PCT No.: PCT/IB2015/000485
§ 371 (c)(1),
(2) Date: Oct. 20, 2017

(87) PCT Pub. No.: WO2016/147021
PCT Pub. Date: Sep. 22, 2016

(65) Prior Publication Data
US 2018/0133264 A1    May 17, 2018

(51) Int. Cl.
*A61K 35/644* (2015.01)
*A61K 36/81* (2006.01)
*A61P 11/06* (2006.01)
*A61P 11/08* (2006.01)

(52) U.S. Cl.
CPC ............ *A61K 35/644* (2013.01); *A61K 36/81* (2013.01); *A61P 11/06* (2018.01); *A61P 11/08* (2018.01)

(58) Field of Classification Search
None
See application file for complete search history.

(56) References Cited

PUBLICATIONS

Bosch, C.H. (2008. Solanum Coagulans. In: Schmelzer, G.H. & Gurib-Fakim, A. (Editors). Plant Resources of Tropical Africa 11(1). Medicinal plants 1. PROTA Foundation, Wageningen, Netherlands/Backhuys Publishers, Leiden, Netherlands/CTA, Wageningen, Netherlands. pp. 521-522).*
"Nightshade"—https://www.britannica.com/plant/nightshade—accessed Feb. 5, 2020.*
Tasleem (J Ayub Med Coll Abbottabad (2011), vol. 23, No. 2, pp. 26-31).*
Written Opinion of the International Search Authority issued to PCT Application No. PCT/IB2015/000485 dated Jan. 11, 2016.
International Search Report issued to PCT Application No. PCT/IB2015/000485 dated Jan. 11, 2016.

* cited by examiner

*Primary Examiner* — Susan Hoffman
(74) *Attorney, Agent, or Firm* — Hackler Daghighian Martino & Novak

(57) ABSTRACT

An herbal remedy to asthma comprising a weighed proportional mixture of Sunnut honey and powder of ground seeds of Solarium dubium. Separation and isolation of active compounds from the methanolic extract of combination was carried out using bioassay-guided fractionation. The in-vivo experiments were implemented to assess the toxicological study of the crude and methanolic extracts of the combination, honey and the seeds. The results revealed that there is no acute or sub-chronic toxicity displayed by the different concentrations of the extracts. The method of Carrageenan induced paw edema in Wister Rats was done to evaluate the anti-inflammatory effects of aqueous crude extract of S. dubium seeds, honey and combination. The results showed that all ingredients were found to have a significant anti inflammatory activity on paw edema volume. Also the result of methanolic extracts showed a significant inhibition of inflammation, As a clinical trial for the combined ingredients, twenty five patients medically diagnosed as asthmatic were randomly selected and enrolled in the study; none of them is currently using anti-asthmatic drugs. Signs of asthma disappeared in the treated patients.

14 Claims, No Drawings

SOLANUM DUBIUM SEEDS AND HONEY (EXTRACTED FROM BEE HIVES IN ACACIA TREE POPULATED AREA) COMBINATION FOR TREATMENT OF ASTHMA AND BRONCHIAL ASTHMA

RATIONALE OF INVENTION

Asthma is an airway disease that can be classified physiologically as a variable and partially reversible obstruction to air flow, and pathologically with overdeveloped mucus glands, airway thickening due to scarring and inflammation, and bronchoconstriction, the narrowing of the airways in the lungs due to the tightening of surrounding smooth muscle. Bronchial inflammation also causes narrowing due to edema and swelling caused by an immune response to allergen. Inflamed airways and bronchoconstriction in asthma, airways narrowed as a result of inflammation response cause wheezing.

The herbal products today symbolize safety in contrast to the synthetics that are regarded in most cases as unsafe to human and environment. Although herbs had been priced for their medicinal, flavoring and aromatic qualities for centuries, the synthetic products of the modern age surpassed their importance, for a while. However, the blind dependence on synthetics is over and people are returning to the naturals with hope of safety and security. Thus the invention is composed of:

A mixture of honey and *Solanum dubium* seeds.

Plant: Kingdom Plantae-plant, Family Solanaceae, Genus *Solanum* and Species *Solanum dubium* Fresen. The plant stems were the collected samples from Alhalfia. Khartoum North. The cleaned and shade-dried plant seeds were fine powdered using a grinding machine. The honey material used is known as Sunnut honey from *Acacia nilotica* (Mimosaceae) Sudan Origin from Bees kingdom Company. The ratio used is 500 g Sunnut honey to 2 g *S. dubium* grounded seeds powder. The mixture is kept for 12 days in a sealed glass stored at room temperature (18-25° C.) in the absence of light. After then the mixture can be kept at room temperature under normal light. The asthmatic patients should take two doses of 10 ml each per day for 20 to 25 days. The first dose should be taken at an empty stomach early in the morning, while the second one to be taken at night. Medicament for asthma may be taken concurrently with this treatment.

Phytochemical analysis of *Solanum dubium* seeds, honey and their combination:

Crude extracts of the seeds of the plant (Sukhdev, et al. 2008), honey and their combination were investigated before and after storage period for their chemical composition (AOAC, 1984), the extracts were screened for phytochemical constituents, Unsaturated Sterols and Triterpenses, Alkaloids, Flavonoids, Tannins, Saponins, cyanogenic glycoside, Anthraquinone glycoside, Cumarins (Martinez and Valencia, 1999; Sofowora 1993; Harborne 1984, 1988; Harborne and Baxter 1993; Wall, et al. 1952) with many few modifications.

Separation and isolation of active compounds from the crude and methanolic extract of combination was carried out using bioassay-guided fractionation. Selection of the active fractions for further fractionation was carried out. Assessment of the results of the extracts for further investigation was based on its pharmacological activity. The combination was extracted with maceration using solvents with different polarities. (Successive extraction with solvents increasing in polarity) Extraction was carried out for about three days for each solvent with daily filtration and evaporation the solvents under reduced pressure using rotary evaporator apparatus. Extract of each solvent were allowed to air till completed dryness and the yield percents were calculated. The methanolic extract was selected for further fractionation based on anti-inflammatory results. Fractionation and isolation of the active ingredients of the methanolic extract were performed by Column Chromatography (Furniss, et al. 1979). The fractions were collected and monitored with thin layer chromatography on silica gel ($GF_{254}$) using different solvent systems (Stalh, 1969). The plates were detected under $UV_{254}$ and sprayed with vanillin sulphuric acid. Plates containing similar spots were combined, together and allowed to dry and then weighed RF values of separated spots were calculated as follows. Distant crossed by spot/distant crossed by solvent front.

After testing the obtained fractions using anti-inflammatory activity, the fractions with potential activity were subjected to preparative thin layer chromatography (Stalh 1969) for more purification, preparative thin Layer Chromatography (PTLC) giving 18 fractions.

Recrystallization techniques were used in fractionation and isolation of pure compounds. Various techniques including nuclear magnetic resonance (NMR), mass spectrometry (MS), ultraviolet (UV) and infrared (IR) spectrometry were used for structure elucidation of the isolated compounds.

Pharmacological activities of *Solanum dubium* seeds, honey and their combination:

In vivo Toxicity:

The in-vivo experiments implemented are to assess the toxicological study of the crude and methanolic extracts of the combination, honey and the seeds on 96 Wister Albino rats. The toxicity of S. dubium seeds, combination and honey in terms of biochemical, hematological and liver and kidney functions in animals using the acute toxicity ($LD_{50}$ percentage) done on 7-days at doses of 2 ml, 10 ml, 20 ml, 40 ml/kg/day body weight respectively via the oral route. The treated animals were monitored for seven days for mortality rate (Ramirez, et al. 2007) and the sub-chronic study was performed with the aqueous extract of the combination at a dose of 2 ml/kg/day and 4 ml/kg/day, via the oral route for 4 weeks. The animals were observed daily for any changes in behavior and manifestations of toxic symptoms. The body weights were recorded every week. At the end of all experimental periods, animals from each group were killed under diethyl ether anesthesia to identify gross lesions and specimens of the liver, intestines, kidneys, spleen and heart were immediately fixed in 10% neutral buffered formalin and processed for histopathology. (Blood samples were collected from the cervical blood vessels of each rat for serum analysis and hematology before the start of the experiment, in the $14^{th}$ and in the $28^{th}$ day respectively (Demma, et al. 2007; Tchamadeu, et al. 2011). The doses of crude extract of combination did not cause mortality or any sign of acute toxicity in all rats dosed for seven days. The extracts were found to be safe up to 2000 mg/kg body weight.

The results revealed that there is no acute or sub-chronic toxicity displayed by the applied different concentrations of the extracts.

Anti-inflammatory Activity:

And anti-inflammatory study of aqueous crude extract of *S. dubuim* seeds, honey and *S. dubuim* seeds and honey (combination) on Wister Rats (42 rats), done to evaluate the anti inflammatory effects in animals using the method of Carrageenan induced paw oedema. (Nayak and Patel, 2010).

The first group serve as control and receive normal saline (1 ml/kg, orally), the second group served as standard and were administrated standard drug diclofenac sodium (100 mg/kg i.p.). The remaining groups were treated with, the third group received honey (2 ml/kg, orally), the fourth group are treated with the S. dubium seeds (2 ml/kg orally), the fifth group are treated with combination (2 ml/kg orally), the sixth group are treated with combination (4 ml/kg orally) and group seventh treated with standard drug hydrocortisone (40 mg/kg i.p.). A mark was made on both the hind paws just below the tibio-tarsal junction. After 30 min of the above treatment an inflammatory oedema was induced in the left hind paw by inject 0.1 ml solution of Carrageenan, in the planter tissue of all the animals. The paw volume was measured at first hour and followed every hour till the fifths hour after administration of carrageenan of each group. The difference between the initial and subsequence reading gave the actual edema volume. The results of the anti inflammatory activity of crude extract of combination 2 ml/kg, combination 4 ml/kg, S. dubium seeds 2 ml/kg and honey 2 ml/kg, showed that all groups were found to have a significant anti inflammatory activity on paw edema volume with increasing of hours from one to five compared with the normal saline control and standard drug diclofenac Sodium. 100 mg/kg. The activity resided more at the higher dose of 4 ml/kg of combination with 91.16% inhibition after 4 hour of extract administration. Also in regard to the other doses 2 ml/kg of combination, 2 ml/kg of S. dubium seeds and 2 ml/kg honey were found to have a significant decrease with 81.05, 72.07 and 66.75% respectively after 4 hour of extract administration when compared with standard drug which was 74.34%. On the other hand, the highest activity was found in 2 ml/kg combination with 96.59% inhibition after 5 hour of extract administration. Also anti-inflammatory activity of all extracts were found to have the values higher than the standard drug hydrocortisone 40 mg/kg (70.39%, 76.35% reduction in edema volume after 4 hour and after 5 hour respectively). The results of the anti-inflammatory activity of successive extracts, all groups showed a significant inhibition of inflammation. Of all the methanolic extract 2 ml/kg showed a significant inhibition of inflammation over the other alcoholic extracts (96.59%).

Also the result of anti-inflammatory Activity of methanolic extracts of combination, S. dubium seed and honey on (36) Wister Rats, the methanolic extract of all groups showed a significant inhibition in inflammation. Of all the alcoholic extracts, the dose of S. dubium seeds 2 ml/kg showed a significant inhibition of inflammation over the other alcoholic extracts (96.9%) and then the combination 2 ml/kg (90.9%). Also the alcoholic extract of all groups decreased rat paw edema.

Finally the results of the anti-inflammatory activity of the fractions of methanolic extract (144) Wister Rats. All fractions showed a significant inhibition in inflammation. The alcoholic extracts of five fractions showed a significant inhibition of inflammation over the other alcoholic fraction extracts. Also the alcoholic extract of all fractions decreased rat paw edema at the end of $5^{th}$ hour. The paw volume was measured initially at 0, 1, 2, 3, 4 and 5 h after Carrageenan injection using digital paw edema meter. Percent inhibition of inflammation was calculated using the formula:

% Inhibition=100(1−vt/vc).

Where (vc) represents edema volume in control and (vt) edema volume in group treated with sample.

Bronchodilator Activity:

The bronchodilator activities of aqueous crude extract of S. dubuim seeds, honey and combination using in vitro studies on isolated tracheal preparations of Guinea pigs (Thirty Guinea pigs weighting (200-250 g)) and Guinea pigs pattern of allergic asthma setup experiment (Kalpana, et al. 2008; Joskova, et al. 2011).

Guinea pigs were randomly divided into three experimental groups. Two groups were actively sensitized by allergen. There were six animals in each group 1 (control group) and group 2 (sensitized group). Group 3 contained 18 Guinea pigs (sensitized and treatment groups) which divided into subgroups each contained 6 guinea pigs (subgroup for seeds extract treatment; subgroup for honey treatment: subgroup for combination extract treatment).

The animals of group 1 received 0.5% Sodium carboxymethyl cellulose (CMC) for 14 days. The animals of group 2 and group 3 were sensitized with egg albumin (1 mL, 10% w/v, i.p.) on the first day. The animals of subgroups 3 were administrated with aqueous crude extract of S. dubium seeds and honey (combination) 2 ml/kg, p.o., once daily for 14 days suspended in 0.5% CMC. The egg albumin was used for active sensitization of guinea pigs by intraperitoneal injection on the $1^{st}$ day. The dose was administrated intraperitonealy again during following 14 days. The whole exposure by this allergen lasted 14 days. Animals were used for the experiment after the end of sensitization.

After the end of sensitization the experiments were actualized. Animals were sacrificed for 90 min., the responses of the trachea to histamine was recorded, the contractions were recorded on Universal Harvard Oscillograph paper using isometric transducer.

Changes in the reactivity of the tracheal smooth muscle dipped into the organ bath with Krebs-Henseleit solution were measured as the reaction on a single dose of bronchoconstrictor mediator histamine ($10^{-8}$ mol.$1^{-1}$). Constant conditions were maintained (temperature, pH). Combination ($10^{-3}$ moL.$1^{-1}$) was added into organ bath with tracheal isolation of trachea. Guinea pigs were stunned by a sharp blow on the head and sacrificed by cutting neck blood vessels. The trachea was rapidly dissected free of surrounding tissues and placed in Petri dish containing oxygenated Krebs-Henseleit solution. Tracheal strips were prepared by cutting the trachea spirally and was suspended in bath tube containing Krebs-Henseleit solution at 37±1° C. under a uniform tension of 1.5 g, continuously bubbled with 95% $O_2$ and 5% $CO_2$ after an initial equilibration period of strips in the third group 30 minutes before mediators with some modifications (Kalpana, et al, 2008; Joskova, et al. 2011).

The results of bronchodilator activities of aqueous crude extract of S. dubuim seeds, honey and S. dubuim seeds and honey (combination), the animals of group 1 (control group) prior administration of the S. dubuim seeds and honey (combination), 1 mg/ml partially blocked the contracting effect of histamine 100 nano g/ml on isolated tracheal spirally cut strip. The S. dubuim seeds extract alone produced further transient stimulant effect followed by persistant relaxant effect on histamine contracting effect on isolated guinea pigs tracheal strip. In animals of group 2 (sensitized group), the S. dubuim seeds and honey (combination), and seeds extract 1 mg/ml relaxed effectively the stimulant effect of the tracheal strip. The relaxant effect of the S. dubuim seeds and honey (combination), was completely blocked by propranolal. The animals of group 3 (sensitized and treatment subgroups), both honey and the S. dubuim seeds and honey (combination), antagonized the contracting effect of histamine 100 nano g/ml on guinea pigs tracheal strip.

Clinical Trials:

The encouraging positive results of the in-vitro and in-vivo phytochemical and pharmacological work on *Solanum dubium* seeds, honey and their combination offered potential benefits which warranted for a pilot clinical study for the application of the above-mentioned herb in patients suffering from chronic bronchial asthma. Twenty five patients medically diagnosed as asthmatic were randomly selected and enrolled in the study; sixteen were males and nine were females. All patients were-above 15 and under 60 years old. Clinical data were collected by direct interview using a structured questionnaire. The study was conducted in two clinics in Khartoum-Sudan from the year 2012 to 2014.

All—the 25 patients who presented to the clinics, had similar complaints, such as: chest tightness, wheeze, breathlessness on exertion. 20% of the patients had a family history of bronchial asthma; none of the patients had a relevant occupational history. All patients were using anti asthmatic drugs; 60% were using occasionally inhaled short-acting $B_2$—a drenoceptor agonists. 24% were using low-dose inhaled steroids. 16% were using, in addition to the inhaler oral bronchodilator therapy. All patients enrolled in the said study were given the mixture of the *Solanum dubium* seeds and honey. They were advised to take a dose of 20 ml twice daily for 25 days. Patients were also advised not to stop the anti-asthmatics which they used to take. Such anti asthmatic drugs could well be used concurrently when necessary. All patients given the combination of the herb and honey were followed up during the first 25 days, and then afterwards for periods, ranging from one to two years. Signs of asthma disappeared in the treated patients. None of them is using anti asthmatic drugs. They are feeling happy and they are leading normal life.

Statistical Analysis:

The program Statistical Package for the Social Sciences (SPSS) version 20 was used to analyze the data. The results were presented in form of both frequency and percentage tables and graphical presentation where required.

REFERENCES

A.O.A.C., 1984. Official methods of Analysis (14th ed). Williams, S. (ed) Association of Official Analytical chemists, Washington, D.C., pp: 152-164.

Demma J., Geber-Miriam T., Asres K., Ergetie W. and Engdawork E. 2007. Toxicological Study on Glinuslotides: a traditionally used taenicial herb in Ethiopia. Journal of Ethnopharmacology. 22; 111 (3) 451-7.

Furniss, B, S. Hannaford, A. J., Smith. P. W. G. and Tatchell, A. R. 1979; Vogels, textbook of practical organic chemistry.

Harborne J. B. 1984. Phytochemical methods. 2nd edition. Chapman and Hall.

Harborne J. B. 1988. Phytochemical Methods—Guide to Modern Techniques of Plant Analysis—$2^{nd}$ Edition—Chapman and Hall.

Harbone J. B., Baxter H. H. 1993. Phytochemical Dictionary: A hand Book of Bioactive Compound from plants. Taylor and Francis; Washington. P. 237.

Joskova M., Franova S. and Sadlonova, V. 2011. Acute bronchodilator effect of quercentin in experimental allergic asthma. Bratislleklisty; 112 (1), pp. 9-12.

Kalpana G., Patel, Payal N., Bhalodia, Ankita D., Patel, Kirti V., Patel and Tejal R. Gandhi, 2008. Evaluation of Bronchodilator and Anti-Anaphylactic Activity of Myricasapida. Iranian Biomedical Journal 12 (3): 191-196.

Martinez A., Valencia G.: Marchafitoquimica. 2003. In Manual de prácticas de Farmacognosia y Fitoquimica: 1999. 1. st edition. Medellin: Universidad de Antioquia; Phytochemical screening methods 59-65.

Nayak B. S. and Patel, K. N. 2010. "Anti-inflammatory screening of *Jatropha Curcas* root, stem and leaf in Albino rats" ROM. J. Biol-Plant-Biol., V. 55, N° 1, pp. 9-13.

Ramirez J. H., Papacies M., Tamayo O., Jaramillo R., and Gutierrez O. 2007. Acute and Subacute Toxicity of *Salvia Scuttlellarioides* in mice and rats. J. Ethnophorm. 19, 109, (2):348-53.

Sofowora A. 1993. Medicinal Plants and Traditional Medicines in Africa. Chichester John, Willey and Sons New York 256.

Stalh E. 1969. Thin Layer Chromatography—First Edition—Springer Verlage—New York. Pages, 200-272.

Sukhdev. S. H; Suman. P. S. K; Gennaro L. and Dev. D. R 2008. Extraction technologies for medicinal and aromatic plants. United Nation Industrial Development Organization and the International Center for Science and High Technology. p 116.

Tchamadeu M. C., Dzeufiet P. D., Nana P., KouambouNouga C. C., NgueguimTsofack F., Allard J., Blaes N., Siagat R, Zapfack L., Girolami J. P., Tack I., Kamtchouing P. and Dimo T. 2011. Acute and sub-chronic oral toxicity studies of an aqueous stem bark extract of Pterocarpussoyauxii-Taub (Papilionacese) in rodents. J. Ethnopharmacol. 27; 133 (2):329-35.

Wall M. E., Eddy C. R, McClenna M. L and Klump M. E. 1952. Detection and estimation of steroid and sapogenins in plant tissue. Analytical Chemistry 24:1337-1342.

CONTENT

Description of the invention
Name of the invention.
Rationale of invention.
Phytochemical analysis of *Solanum dubium* seeds, honey and their combination
Pharmacological activities of *Solanum dubium* seeds, honey and their combination
   In vivo toxicity
   Anti-inflammatory activity
   Bronchodilator activity
   Clinical trials
Statistical analysis
References

The invention claimed is:

1. A composition consisting essentially of an effective amount of an orally administrable mixture of honey derived from the flowers of *Acacia nilotica* and seed powder of the species *Solanum dubium* of the Solanaceae family, wherein the honey to seed powder ratio is 500 g of honey to 2 g of seed powder.

2. The orally administrable composition of claim 1, wherein the effective amount is at least 2 ml/kg of body weight but no greater than 2000 ml/kg of body weight.

3. The orally administrable composition of claim 1, wherein the effective amount is in the range of about 2 ml/kg of body weight to about 4 ml/kg of body weight.

4. The orally administrable composition of claim 1, wherein the effective amount of the orally administrable composition is 20 ml administered twice daily.

5. A composition comprising: an effective amount of an orally administrable mixture of honey and seed powder of the species *Solanum dubium* of the Solanaceae family, wherein the honey is derived from the flowers of *Acacia nilotica* and wherein the honey to seed powder ratio is 500 g of honey to 2 g of seed powder.

6. The composition of claim 5, wherein the effective amount is at least 2 ml/kg of body weight but no greater than 2000 ml/kg of body weight.

7. The composition of claim 5, wherein the effective amount is in the range of about 2 ml/kg of body weight to about 4 ml/kg of body weight.

8. The composition of claim 5, wherein the effective amount is 20 ml.

9. A therapeutic solution for the treatment of asthma, the therapeutic solution consisting of an effective amount of an orally administrable mixture of honey derived from the flowers of *Acacia nilotica* and seed powder of the species *Solanum dubium* of the Solanaceae family, wherein the honey to seed powder ratio is 500 g of honey to 2 g of seed powder.

10. The therapeutic solution of claim 9, wherein the effective amount is at least 2 ml/kg of body weight but no greater than 2000 ml/kg of body weight.

11. The therapeutic solution of claim 9, wherein the effective amount is in the range of 2 ml/kg of body weight to 4 ml/kg of body weight.

12. The therapeutic solution of claim 9, wherein the effective amount is 10 ml administered twice daily.

13. The therapeutic solution of claim 9, wherein the effective amount is 20 ml administered twice daily.

14. The therapeutic solution of claim 9, wherein the asthma is bronchial asthma.

* * * * *